US009751815B2

(12) United States Patent
Silks et al.

(10) Patent No.: US 9,751,815 B2
(45) Date of Patent: *Sep. 5, 2017

(54) CONVERSION OF OLIGOMERIC STARCH, CELLULOSE, HYDROLYSATES OR SUGARS TO HYDROCARBONS

(71) Applicant: Los Alamos National Security, LLC, Los Alamos, NM (US)

(72) Inventors: Louis A. Silks, Los Alamos, NM (US); Andrew Sutton, Los Alamos, NM (US); Jin Kyung Kim, Los Alamos, NM (US); John Cameron Gordon, Los Alamos, NM (US); Ruilian Wu, Los Alamos, NM (US); David B. Kimball, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/284,378

(22) Filed: Oct. 3, 2016

(65) Prior Publication Data

US 2017/0022122 A1 Jan. 26, 2017

Related U.S. Application Data

(63) Continuation-in-part of application No. 14/413,552, filed as application No. PCT/US2012/055337 on Sep. 14, 2012, now Pat. No. 9,469,574.

(60) Provisional application No. 61/669,980, filed on Jul. 10, 2012.

(51) Int. Cl.
  *C07D 407/06* (2006.01)
  *C07C 1/207* (2006.01)

(52) U.S. Cl.
  CPC .......... *C07C 1/2076* (2013.01); *C07D 407/06* (2013.01); *C07C 2521/18* (2013.01); *C07C 2523/44* (2013.01); *C07C 2523/755* (2013.01)

(58) Field of Classification Search
  None
  See application file for complete search history.

(56) References Cited

U.S. PATENT DOCUMENTS

| 9,469,574 B2* | 10/2016 | Silks ................. C10G 3/47 |
| 2009/0139134 A1 | 6/2009 | Yoshikuni et al. |
| 2010/0228067 A1 | 9/2010 | Peterson et al. |
| 2011/0312050 A1 | 12/2011 | Zhang et al. |
| 2011/0312487 A1 | 12/2011 | Chen et al. |
| 2011/0312488 A1 | 12/2011 | Chen et al. |

OTHER PUBLICATIONS

Blommel et al., "Oligosaccharide Oligosaccharide Oligosaccharide", Aug. 25, 2008, retrieved from http://www.biofuelstp.eu/downloadsNirent_Technology_Whitepaper.pdf.

* cited by examiner

*Primary Examiner* — Tam M Nguyen
(74) *Attorney, Agent, or Firm* — Lewis Roca Rothgerber Christie LLP

(57) ABSTRACT

Embodiments of the present invention are directed to the conversion of a source material (e.g., a depolymerized oligosaccharide mixture, a monomeric sugar, a hydrolysate, or a mixture of monomeric sugars) to intermediate molecules containing 7 to 26 contiguous carbon atoms. These intermediates may also be converted to saturated hydrocarbons. Such saturated hydrocarbons are useful as, for example, fuels.

19 Claims, 1 Drawing Sheet

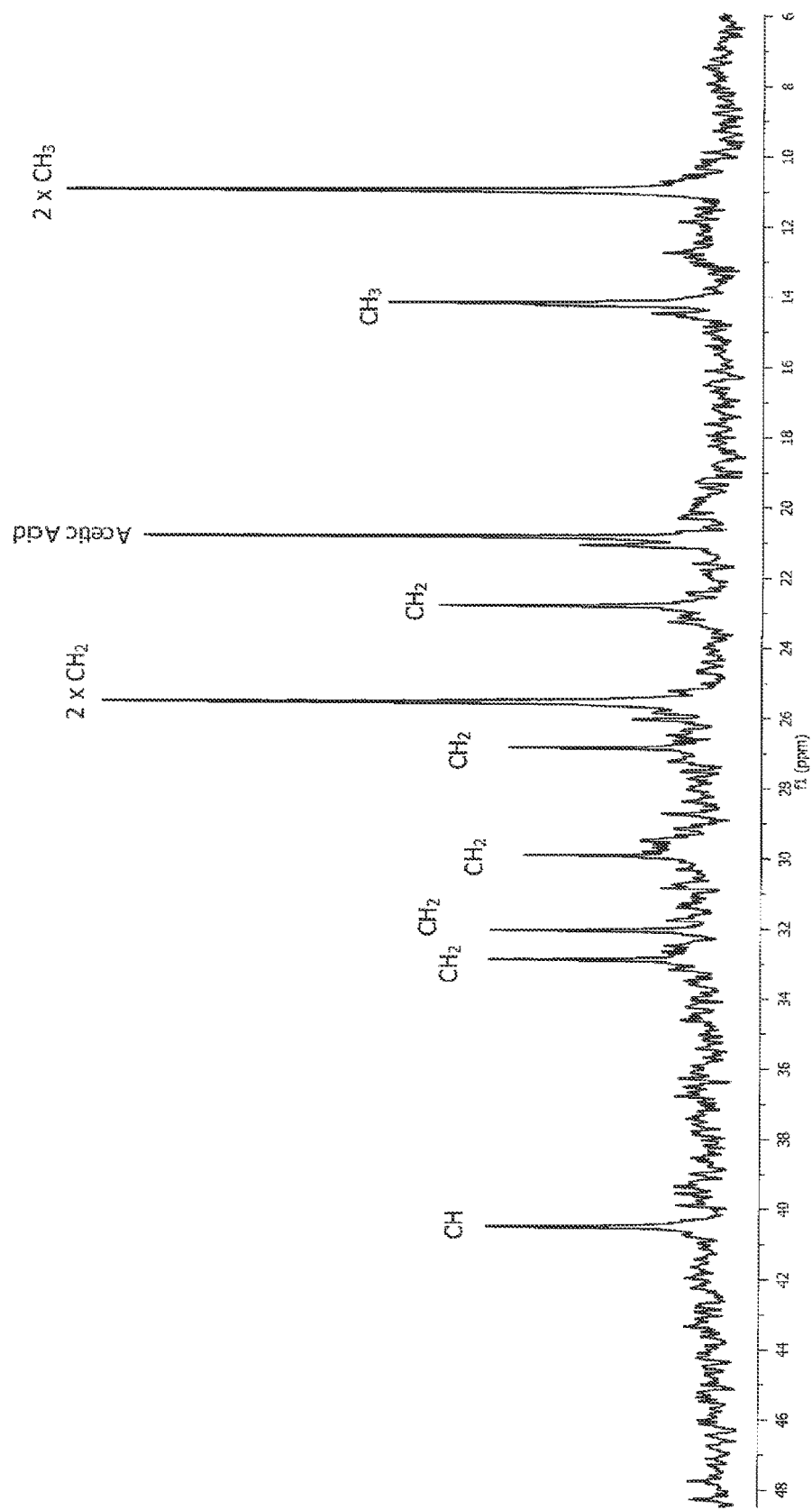

CONVERSION OF OLIGOMERIC STARCH, CELLULOSE, HYDROLYSATES OR SUGARS TO HYDROCARBONS

CROSS-REFERENCE TO RELATED APPLICATION(S)

This application is a continuation-in-part of U.S. patent application Ser. No. 14/413,552 filed Sep. 14, 2012, now U.S. Pat. No. 9,469,574, which is a national phase of International Application No. PCT/US2012/055337 filed Sep. 14, 2012, which claims priority to and the benefit of U.S. Provisional Application Ser. No. 61/669,980 filed Jul. 10, 2012, the entire contents of all of which are incorporated herein by reference

STATEMENT REGARDING FEDERALLY SPONSORED RESEARCH OR DEVELOPMENT

The United States government has rights in this invention pursuant to Contract No. DE-AC52-06NA25396 between the United States Department of Energy and Los Alamos National Security, LLC for the operation of Los Alamos National Laboratory.

TECHNICAL FIELD

Embodiments of the present invention are directed to the selective conversion of starch, cellulose, hydrolysates and/or monomeric sugars (such as, e.g., glucose or xylose) to molecules containing 7 to 26 contiguous carbon atoms. In some embodiments, the process also includes the conversion of the intermediates to saturated hydrocarbons. Such saturated hydrocarbons are useful as, for example, fuels.

BACKGROUND

Saturated hydrocarbons containing from about seven to about sixteen carbons, up to about twenty-six carbons, are used as fuels, as well as other materials. Such hydrocarbons are typically extracted or generated from petroleum, a non-renewable resource. Methods of generating fuel- and high-quality hydrocarbons from renewable sources are thus needed.

SUMMARY

Embodiments of the present invention are directed to processes for preparing saturated hydrocarbons. In some embodiments, for example, a process for preparing saturated hydrocarbons includes chain extension of a source material and hydrodeoxygenation of the resulting intermediate. The source material may be any suitable source material, and in some embodiments, the source material includes a source of one or more sugars, which may be present in the form of a monomeric sugar, a hydrolysate (or a mixture of sugars and/or acids), or a mixture of monomeric sugars. In some embodiments, the method may further include depolymerizing or deoligomerizing a precursor material to form the source material. For example, in some embodiments, the method may include heating an oligosaccharide (as a precursor material) under acidic conditions for a time sufficient to form a depolymerized oligosaccharide mixture as the source material.

According to some embodiments, the process for preparing saturated hydrocarbons may include adding a suitable metal catalyst and a dicarbonyl to the source material under conditions to yield an intermediate mixture, and adding hydrogen and a suitable hydrogenation catalyst to said intermediate mixture under suitable conditions to yield the saturated hydrocarbon.

BRIEF DESCRIPTION OF THE DRAWINGS

FIG. 1 depicts the NMR spectra from an unpurified product of example 2(a), an embodiment of the invention.

DETAILED DESCRIPTION OF ILLUSTRATIVE EMBODIMENTS

According to embodiments of the present invention, a process for preparing saturated hydrocarbons includes chain extension of a source material to form an intermediate, and hydrodeoxygenation of the intermediate to form one or more saturated hydrocarbons. The source material may be any suitable source material, and in some embodiments, the source material includes a source of one or more sugars, which may be present in the form of a monomeric sugar, a hydrolysate (or a mixture of sugars and/or acids), or a mixture of monomeric sugars.

As used herein, the term "hydrolysate" is used in its art-recognized sense to refer to the enzymatic hydrolysis product of a starting material. Indeed, as would be understood by those of ordinary skill in the art, the term "hydrolysate" refers to the mixture of sugars that results from the enzymatic hydrolysis (or breaking down) of a more complex starting material. As would also be understood by those of ordinary skill in the art, the starting material from which a hydrolysate may be formed may include, for example, cellulose, lignocellulose, hemicellulose or the like. Additionally, the starting material from which the hydrolysate is obtained may be sourced from any suitable biomass or agricultural source (some nonlimiting examples of which include corn stover and potatoes). Some nonlimiting examples of suitable hydrolysates include mixtures of different sugars, for example glucose, xylose, arabinose, cellobiose, galactose and/or fructose. In some embodiments, the hydrolysate may further include one or more acids, for example one or more organic acids. Some nonlimiting examples of such organic acids include lactic acid, glycerol, ethanol, acetic acid, ethanol, furfural and hydroxymethylfurfural (HMF).

In contrast, the terms "mixture of monomeric sugars" and "simple mixture of monomeric sugars" (and like terms) refer to a mixture of sugars that is not obtained from a hydrolysis process. Instead, the "mixtures" of monomeric sugars are obtained by simply mixing different monomeric sugars, which may be obtained from the same or different sources.

In some embodiments, the source material may be obtained from a precursor material, which is first processed into a suitable source material for chain extension. For example, in some embodiments, the precursor material may include an oligosaccharide. Oligosaccharides such as starch, cellulose, hemicelluloses, chitin, and cotton are abundant and easily obtainable materials that can be potentially used as precursors for fuels and chemical feedstocks. But to access the sugar molecule building blocks (as the source material), e.g., 5- or 6-carbon containing units, located within these biopolymers and to transform them into useful fuel precursors, depolymerization followed by the chain extension is needed. Embodiments of the present invention are directed to methods for readily performing these transformations.

According to embodiments of the present invention, a suitable oligosaccharide can be used as a suitable precursor material and ultimately converted to a saturated hydrocarbon in a process, with or without isolation of the intermediate products. In one aspect of the present invention, the process of converting an oligosaccharide precursor material to a saturated hydrocarbon is achieved in a single pot or reaction vessel without isolation of any intermediate products.

As used herein, "saturated hydrocarbon" refers to organic compounds comprising saturated, straight or branched chain alkane moieties. In some embodiments, the saturated hydrocarbons may include 7-26 carbon atoms, for example 7-16 carbon atoms. One nonlimiting example of a saturated hydrocarbon is 3-ethylnonane.

As used herein, "intermediate mixture" refers to a compound or mixture of compounds derived from processes according to embodiments of the invention, e. g., the intermediate reaction products resulting from the combination of the source material (e.g., a monomeric sugar, hydrolysate, mixture of monomeric sugars, or depolymerized oligosaccharide mixture) with one or more dicarbonyls. The intermediate mixtures according to embodiments of the invention can contain 7 to 26 contiguous carbon atoms, for example, 7-16 contiguous carbon atoms. Within the scope of embodiments of the invention, intermediate mixtures can also include additional moieties, for example, esters. The addition of such moieties does not contribute to the contiguous carbon count of the resulting saturated hydrocarbons according to embodiments of the invention.

As used herein, "starch" refers to an oligosaccharide comprising glucose units.

As used herein, "triflate", also referred to as trifluoromethanesulfonate, is a group with the formula $[CF_3SO_3]^-$. As used herein, the group $[CF_3SO_3]^-$ may also be designated as "OTf."

As used herein "oligosaccharides" are compounds including more than one saccharide molecule. Oligosaccharides within the scope of embodiments of the invention include starch, cellulose, hemicelluloses, glucose, cellobiose, chitin, and cotton. "Oligosaccharides" according to embodiments of the invention also include compounds comprising monomeric building blocks derived from sugars such as 2-amino glucose, galactose, xylose, and the like. Disaccharides are within the scope of the oligosaccharides according to embodiments of the invention.

As used herein, "Lewis acids" are substances that are electron-pair acceptors. Lewis acids are known in the art and some nonlimiting examples include $La(OTf)_3$, $Fe(OTf)_3$, $CeCl_3$, $ZnCl_2$, $ZrCl_4$, $BiCl_3$, $Sc(OTf)_3$, $Y(OTf)_3$, $La(OTf)_3$, and $Fe(OTf)_3$.

As used herein, "Bronsted acids" are substances that are able to donate a proton. Examples of Bronsted acids are known in the art.

According to embodiments of the present invention, a precursor material (e.g., an oligosaccharide, for example, starch) may be heated under conditions to yield a depolymerized oligosaccharide mixture. Such heating can be provided by, for example, heating at reflux or by microwave heating. The heating may be conducted under acidic conditions such as those provided by the addition of dilute hydrochloric acid, triflic acid, acetic acid, trifluoroacetic acid, or a combination thereof. Lewis acids or Bronsted acids can also be added to the heating step. Use of mixtures of acids during the heating step to form the depolymerized oligosaccharide mixture is also within the scope of embodiments of the invention.

Alternatively, thermally stable amylases or cellulases, or room temperature depolymerization with native enzymes, can be used to depolymerize the precursor material (e.g., the oligosaccharide mixture) to form the source material.

Within the scope of embodiments of the invention, the source material (e.g., the depolymerized oligosaccharide mixture, the monomeric sugar, the hydrolysate, or the mixture of monomeric sugars) may be combined with one or more dicarbonyls to form an intermediate mixture. Nonlimiting examples of suitable dicarbonyls for this purpose include methyl acetoacetate, ethyl acetoacetate (EAA), isopropyl acetoacetate (i-PrAA), 2,4-pentanedione (PD), n-propyl acetoacetate, esters of cyanoacetate, esters of malonate, and the like, as well as mixtures thereof. For example, in some embodiments, 2,4-pentanedione may be used.

The combination of the source material (e.g., the depolymerized oligosaccharide mixture, the monomeric sugar, the hydrolysate, or the mixture of monomeric sugars) with the dicarbonyl to form the intermediate mixture can optionally be conducted in the presence of a catalyst, for example a Lewis acid catalyst or a Bronsted acid catalyst, although any suitable acid catalyst can be used in the processes according to embodiments of the invention. Nonlimiting examples of suitable Lewis acids include Lewis acids of the formula $Ln(X)_n$ where Ln is a lanthanoid; X is a halide, triflate, bis(triflamide), $C_{1-6}$ alkyl, aryl, amine, oxide, $C_{1-6}$ alkoxide, or aryloxide; and n is 2 or 3. For example, some nonlimiting specific examples of the Lewis acid include $La(OTf)_3$ and $Fe(OTf)_3$. Other suitable Lewis acids for use in embodiments of the invention include $CeCl_3$, $ZnCl_2$, $ZrCl_4$, and $BiCl_3$. According to some embodiments, the Lewis acid may also include a rare earth triflate. Nonlimiting examples of rare earth triflates include $Sc(OTf)_3$, $Y(OTf)_3$, and $La(OTf)_3$. For example, in some embodiments, lanthanum triflate may be used. In some embodiments, the triflate may be $Fe(OTf)_3$. Additional Lewis acids may be used in embodiments of the present invention and are well known to those skilled in the art.

The combination of the source material (e.g., the depolymerized oligosaccharide mixture, the monomeric sugar, the hydrolysate, or the mixture of monomeric sugars) with the dicarbonyl to form the intermediate mixture may also be conducted in the presence of one or more acids, such as, for example, triflic acid (trifluoromethanesulfonic acid) and HCl. Such acids have been found useful in forming the intermediate mixture.

In some embodiments, the formation of the intermediate mixture is achieved in the presence of cerium chloride, iron chloride, indium chloride, bismuth chloride, lanthanum triflate, zirconium triflate, copper triflate, iron triflate, or a mixture thereof. In some embodiments, the formation of the intermediate mixture may be achieved in the presence of cerium chloride, iron chloride, lanthanum triflate, iron triflate, or a mixture thereof.

Conversion from the intermediate mixture to the saturated hydrocarbon(s) can be accomplished by hydrogenation of the intermediate mixture and can be carried out with a suitable hydrogenation catalyst, for example, palladium on carbon (Pd/C) or nickel catalysts (such as, for example, Raney Ni or other nickel derived from a Ni—Al alloy). A suitable acid may also be added. Nonlimiting examples of suitable acids for this purpose include acetic acid, hydrochloric acid and triflic acid. In some embodiments, for example, the acid may include triflic acid or hydrochloric acid. In some embodiments, the reaction mixture be aqueous. Those skilled in the art can readily identify suitable reaction temperatures using routine experimentation. For example, the hydrogenation can be achieved at room temperature or above room temperature. In some embodiments, for example, the hydrogenation reaction can be accomplished at temperatures of about 200° C. to 250° C. under a hydrogen atmosphere.

Some nonlimiting examples of suitable hydrogenation catalysts include those comprising palladium, platinum, iron, cobalt, copper, chromium, nickel, or a mixture thereof. Catalysts comprising these metals are known in the art. Some nonlimiting examples of specific catalysts include Pd/C and Ni (e.g., Raney Ni or other Ni derived from a Ni—Al alloy). The skilled person can determine a suitable amount of catalyst needed to perform the methods according to embodiments of the invention by routine experimentation.

During hydrogenation, the hydrogen can be supplied at either atmospheric pressure or at a pressure above atmospheric pressure. For example, in some embodiments, the hydrogen pressure may be about 15 psi to about 500 psi, for example, about 100 psi. In some embodiments, for example those using a Ni catalyst instead of a Pd/C catalyst, the pressure may be about 200 psi to about 500 psi, for example about 250 psi to about 450 psi, or about 300 psi.

The skilled person can readily determine appropriate temperatures for the reactions in the processes according to embodiments of the present invention without undue experimentation. However, in some embodiments, the temperature may be about ambient temperature to about 250° C. In some embodiments, for example, the temperature for the hydrogenation reactions may be about 200° C. to about 250° C.

Conversion of the Source Material to Branched Alkanes

Coupling can be performed using a variety of source materials (e.g., depolymerized oligosaccharide mixtures, monomeric sugars, hydrolysates, or mixtures of monomeric sugars) and diketones to give the general (furan) intermediate mixture A shown in Scheme 1. Scheme 1 is general and applicable to all combinations of different source materials (e.g., depolymerized oligosaccharide mixtures, monomeric sugars, hydrolysates, or mixtures of monomeric sugars) and diketones. For example, although Scheme 1 indicates an oligosaccharide source material, it is understood that Scheme 1 is equally applicable to other source materials, including depolymerized oligosaccharide mixtures, monomeric sugars, hydrolysates, or mixtures of monomeric sugars. Starch extracted directly from a Russet potato and treated by the procedures of the invention yielded identical products and reactivity.

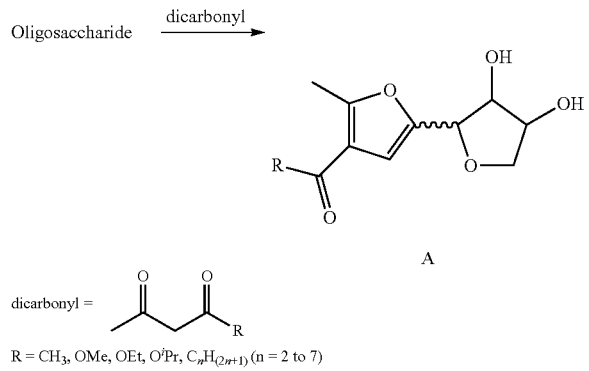

The following examples are illustrative only and are not intended to be construed as limiting of the invention.

Example 1

Preparation of 1-(5-(3,4-dihydroxytetrahydrofuran-2-yl)-2-methylfuran-3-yl)ethanone (1)

A 2-neck round bottom flask equipped with a thermometer and reflux condenser was charged with starch (1.00 g, 9.25 mmol according to molecular weight 162.12) and 0.1 M hydrochloric acid (10.0 mL). The mixture was heated to 90-95° C. for 24 hours. The mixture was removed from heat, and to this was added cerium chloride heptahydrate (0.186 g, 0.500 mmol), EtOH (22.5 mL) and 2,4-pentanedione (0.617 g, 0.63 mL, 6.17 mmol). The mixture was then heated again at 70-75° C. for 48 h. The solvent was removed by rotary evaporation and the residue was purified on silica gel with 50% EtOAc/hexanes to provide 0.890 g (64%) of 1-(5-(3,4-dihydroxy-tetrahydrofuran-2-yl)-2-methylfuran-3-yl)ethanone as a light yellow solid. $^1$H NMR (CDCl$_3$) δ 6.61 (s, 1H), 4.66 (d, J=6.7 Hz, 1H), 4.49-4.33 (m, 2H), 4.27 (dd, J=10.1, 4.7 Hz, 1H), 3.90 (dd, J=10.1, 2.9 Hz, 1H), 2.58 (s, 3H), 2.39 (s, 3H).

Examples 2(a)-2(e)

Conversion of (1) into 3-Ethylnonane

Method (a). Compound (1) (0.200 g, 0.885 mmol) was dissolved in glacial acetic acid (5 mL) and added along with Pd/C (0.100 g, 5 wt. % Pd, 0.005 g Pd, 5.30 mol % Pd) and La(OTf)$_3$ (0.100 g, 0.171 mmol, 19.0 mol % La) to a stainless steel Swagelok sample tube. The tube was then pressurized with 100 psi H$_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over NaSO$_4$ and solvent removed in vacuo to yield 3-ethylnonane as a colorless oil (0.102 g, 85%). $^{13}$C NMR (101 MHz, CDCl$_3$) δ 40.54 (CH), 32.92 (CH$_2$), 32.08 (CH$_2$), 29.94 (CH$_2$), 26.87 (CH$_2$), 25.58 (2×CH$_2$), 22.82 (CH$_2$), 14.20 (CH$_3$), 11.01 (2×CH$_3$). $^1$H NMR (400 MHz, CDCl$_3$) δ 4.10 (m, 1H), 1.25 (m, 14H), 0.82 (m, 9H).

Method (b). Compound (1) (0.200 g, 0.885 mmol) was dissolved in 1M HOTf (5 mL) and added along with Pd/C (0.100 g, 5 wt. % Pd, 0.005 g Pd, 5.30 mol % Pd). The tube was then pressurized with 100 psi H$_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over NaSO$_4$ and solvent removed in vacuo to yield 3-ethylnonane as a colorless oil.

Method (c). Compound (1) (0.200 g, 0.885 mmol) was dissolved in 0.1M HOTf (trifluoromethane sulfonic acid, 5 mL) and added along with Pd/C (0.100 g, 5 wt. % Pd, 0.005 g Pd, 5.30 mol % Pd). The tube was then pressurized with 100 psi H$_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over NaSO$_4$ and solvent removed in vacuo to yield 3-ethylnonane as a colorless oil.

Method (d). Compound (1) (0.200 g, 0.885 mmol) was dissolved in 1M HCl (hydrochloric acid, 5 mL) and added along with Pd/C (0.100 g, 5 wt. % Pd, 0.005 g Pd, 5.30 mol % Pd). The tube was then pressurized with 100 psi H$_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over $NaSO_4$ and solvent removed in vacuo to yield 3-ethylnonane as a colorless oil.

Method (e). Compound (1) (0.200 g, 0.885 mmol) was dissolved in glacial acetic acid (5 mL) and added along with Pd/C (0.100 g, 5 wt. % Pd, 0.005 g Pd, 5.30 mol % Pd) and $Fe(OTf)_3$ (0.100 g, 0.283 mmol) to a stainless steel Swagelok sample tube. The tube was then pressurized with 100 psi $H_2$ and heated to 225° C. for 14 hours. Upon cooling, the pressure was released and reaction mixture extracted from the vessel with methylene chloride (2×1 mL) and water (2×1 mL). The combined layers were filtered and the organic layer separated, dried over $NaSO_4$ and solvent removed in vacuo to yield 3-ethylnonane as a colorless oil.

Example 3

One Pot Preparation of 3-Ethylnonane

A 300 mL stainless steel Parr reactor equipped with a temperature and pressure control system was charged with 1.00 g (9.25 mmol) starch (using a molecular weight of 162.12 g/mol based on the molecular weight of glucose), 20 mL of $H_2O$, and triflic acid (final concentration, 0.1 M). The mixture was stirred and heated to 90-95° C. for 24 hours. Cerium chloride heptahydrate (0.186 g, 0.5 mmol), EtOH (22.5 mL) and 2,4-pentanedione (0.617 g, 0.63 mL, 6.17 mmol) were added and the temperature was maintained at 90-95° C. for 48 h. At this point, Pd/C (0.100 g, 10 wt. % Pd) was added. The mixture was degassed (3.times.) and pressurized with 100 psi $H_2$ and was heated to 225° C. for 14 hours. Upon cooling, the pressure was released and reaction mixture extracted from the vessel with methylene chloride (2×1 mL) and water (2×1 mL). The combined layers were filtered and the organic layer was separated, dried over $NaSO_4$ and solvent removed in vacuo to yield 3-ethylnonane as a colorless oil.

Example 4

Various experimental conditions were employed for the conversion of starch into (furan) intermediate molecules, with results and conditions for the different experimental conditions reported below in Table 2. The general procedure involved combining starch with a metal catalyst (mol % of catalyst relative to dicarbonyl donor) in water, heating this mixture in a microwave reactor to release glucose monomers from the starch polysaccharide chains, then adding a dicarbonyl donor to the reaction and further heating either in the microwave reactor or under reflux. The yields reported in Table 2 are obtained either after product isolation via chromatography or determined directly using liquid chromatography mass spectrometry (LCMS). For the LCMS method, an aliquot is taken from the reaction mixture and combined with a known concentration of $^{13}C_6$ enriched intermediate molecules made independently using $^{13}C_6$ glucose such that comparison of the two molecular ion peaks (M+1 vs. M+7) in the LCMS allows for quantitative determination of product yield.

Tables 2 and 3 demonstrate various outcomes using lanthanum triflate, cerium chloride or iron chloride as catalysts. The dicarbonyl donor was selected from ethyl acetoacetate (EAA), isopropyl acetoacetate (i-PrAA), or 2,4-pentanedione (PD). In some embodiments, the starch may be hydrolyzed prior to condensation with the donor. Good conditions resulted from the combination of 10 mol % $CeCl_3$, EAA, starch (excess; 1.25 equiv), and a microwave reaction temperature of 140° C. for 48 h.

TABLE 2

Depolymerization of starch using a Lanthanide or Fe catalyst, by microwaving at 140° C. for 1.5 h before combining with donor and additional heating.

| Using 1.25 equiv | Donor | Catalyst/ Loading | Conditions | Product Yield |
|---|---|---|---|---|
| Starch | EAA | 2.5% $La(OTf)_3$ | Reflux w EtOH 72 h | 32%, LCMS |
| Starch | EAA | 10% $La(OTf)_3$ | 140° C. 1.5 h w $H_2O$ | 12%, LCMS |
| Starch | EAA | 10% $CeCl_3$ | 140° C. 1.5 h w $H_2O$ | 30%, LCMS |
| Starch | iPrAA | 10% $CeCl_3$ | 140° C. 1.5 h w $H_2O$ | 35%, Isolated |
| Starch | EAA | 10% $CeCl_3$ | Reflux w $H_2O$ 48 h | 40%, LCMS |
| Starch | iPrAA | 10% $CeCl_3$ | Reflux w $H_2O$ 48 h | 35%, LCMS |
| Starch | PD | 25% $FeCl_3$ | Reflux w $H_2O$ 24 h | 15%, Crude |
| Starch | PD | 25% $FeCl_3$ 1st recycle | Reflux w $H_2O$ 24 h | 30%, Crude |

Example 5

Table 3 shows the production of glucose from starch hydrolysis/depolymerization with various lanthanide containing catalysts using a microwave reactor at 140° C. for various durations.

TABLE 3

Conversion of starch to glucose.

| Catalyst/Loading | Conditions | Yield of Glucose |
|---|---|---|
| 2.5% $La(OTf)_3$ | 140 C. 3 h 30 min in $H_2O$ | 51% LCMS |
| 5% $La(OTf)_3$ | 140 C. 3 h in $H_2O$ | 42.2% LCMS |
| 10% $La(OTf)_3$ | 140 C. 3 h in $H_2O$ | 45.6% LCMS |
| 20% $La(OTf)_3$ | 140 C. 3 h in $H_2O$ | 57% LCMS |
| 10% $CeCl_3$ | 140 C. 2 h in $H_2O$ | 55% LCMS |

Example 6

Table 4 illustrates that starch hydrolysis/depolymerization can be performed concurrently with the condensation reaction.

TABLE 4

Results of concurrent starch hydrolysis/depolymerization into glucose and conversion into $C_{11}$ product

| Starting Material | Donor | Catalyst Loading | Temperature | Microwave Time | Total Conversion | Product yield* |
|---|---|---|---|---|---|---|
| Starch | PD | 10 mol % $CeCl_3 \cdot 7H_2O$ | 130° C. | 3.5 hrs | No rxn | |
| Starch | PD | 10 mol % $CeCl_3 \cdot 7H_2O$ | 150° C. | 3.5 hrs | 83% | 33% |
| Starch | PD | 20 mol % $CeCl_3 \cdot 7H_2O$ | 150° C. | 3.5 hrs | NA | |

*product yield determined by NMR spectroscopy

Example 7

Table 5 shows the effect of different concentrations of CeCl₃ and reaction time on yields of products that result from reaction of glucose with EAA or glucose with iPrAA.

TABLE 5

Outcome of reactions of glucose with EAA or glucose with iPrAA in the presence of CeCl₃•7H₂O (catalyst loading relative to Glucose)

| Starting Material | Donor | Catalyst Loading | Temperature | Microwave Time | Total Conversion | Product yield* |
|---|---|---|---|---|---|---|
| Glucose | EAA | 25 mol % CeCl₃•7H₂O | 100° C. | 6.5 hrs | 56% | 41% |
| Glucose | iPrAA | 25 mol % CeCl₃•7H₂O | 100° C. | 6.5 hrs | 72% | 43% |
| Glucose | iPrAA | 25 mol % CeCl₃•7H₂O | 110° C. | 5 hrs | 58% | 48% |
| Glucose | iPrAA | 40 mol % CeCl₃•7H₂O | 100° C. | 4 hrs | 57% | 26% |
| Glucose | iPrAA | 55 mol % CeCl₃•7H₂O | 100° C. | 4 hrs | 50% | 31% |
| Glucose | iPrAA | 25 mol % CeCl₃•7H₂O | 100° C. | 4 hrs | 34% | 22% |
| Glucose | iPrAA | 25 mol % CeCl₃•7H₂O | 100° C. | 4 hrs | 48% | 24% |

*product yields determined from NMR spectra

Example 8

Table 6 shows that starch can be converted in reasonable yields into the corresponding furan intermediates using cerium chloride as the catalyst. Depolymerizing the starch via microwave promotion is carried out first, followed by reflux in the presence of the ketone donor at 97° C. for 48 h. Additionally, when starch isolated from a russet potato was used, coupling with PD resulted in the corresponding C₁₁ adduct in 36% yield (based on the potato containing 50% starch). See Mathews, K. R., Landmark, J. D., Stickle, D. F., J. Chem. Ed. 2004, 81, 702, the entire contents of which are incorporated herein by reference.

TABLE 6

Starch depolymerized in microwave 2 hrs at 140° C., and heat at reflux.

| Using 1.5 equiv | Donor | Catalyst Loading | Total Conversion | Product Yield* |
|---|---|---|---|---|
| Starch | iPrAA | 25 Mol % CeCl₃•7H₂O | 100% | 61% |
| Starch | iPrAA | 50 Mol % CeCl₃•7H₂O | 100% | 68% |
| Starch | iPrAA | Recycled 50 Mol % CeCl₃•7H₂O | 100% | 65% |
| Potato Starch | PD | 25 mol % CeCl₃•7H₂O | 50% | 36% |

*product yields determined by NMR spectroscopy

Example 9

Table 7 shows the effect of conventional heating (i.e. no microwaving) in various solvent and solvent mixtures on the CeCl₃ catalyzed reaction between starch and PD under acidic conditions. A slight excess of starch to PD was used and the product yields are listed as isolated, purified yields.

TABLE 7

Conventional heating of starch in the presence of PD.

| solvent | catalyst | Temperature (24 h) | yield (%) |
|---|---|---|---|
| 0.25M HCl | CeCl₃•7H₂O, Na₂MoO₄ | 80-90° C. | 24 |
| 0.25M HCl | FeCl₃ | 83-85° C. | 5 |
| 0.05% w/w HCl | CeCl₃•7H₂O | 90-95° C. | NR |
| 0.1M HCl—EtOH (1:2) | CeCl₃•7H₂O (9%) | 90-95° C. | 42% |
| 0.25M HCl—EtOH | CeCl₃•7H₂O | 70-75° C. | NR |
| 0.1M HCl | CeCl₃•7H₂O (20%) | 90-95° C. | 17% |
| 0.1M HCl | CeCl₃•7H₂O (8%) | 90-95° C. | 24% |
| 0.1M HCl—EtOH (1:1) | CeCl₃•7H₂O (8%) | 90-95° C. (48 h) | 44% |
| 1M HCl—EtOH (1:1) | CeCl₃•7H₂O (7%) | 90-95° C. | 18% |
| 0.1M HCl—EtOH (1:2) | CeCl₃•7H₂O (8%) | 90-95° C. | 55% |
| 0.1M HCl—EtOH (1:3) | CeCl₃•7H₂O (8%) | 90-95° C. | 33% |
| 0.1M HCl—EtOH (2:3) | CeCl₃•7H₂O (10%) | 90-95° C. | 62% (starch 1.2 eq.) |
| 0.1M HCl | CeCl₃•7H₂O (10%) | 90-95° C. | 29% (starch 1.2 eq.) |
| 0.1M HCl—EtOH (2:3) | CeCl₃•7H₂O (8%) | 90-95° C. | 64% (starch 1.5 eq.) |
| 0.1M HCl—EtOH (1:1) | CeCl₃•7H₂O (8%) | 90-95° C. | 63% (starch 1.5 eq.) |
| 0.1M HCl—EtOH (1.5:1) | CeCl₃•7H₂O (10%) | 90-95° C. | 64% (starch 1.2 eq.) |
| 0.1M HCl—EtOH (2:1) | CeCl₃•7H₂O (10%) | 90-95° C. | 59% (starch 1.2 eq.) |

Example 10

Glucose was reacted with 1.5 equivalents of PrAA, and 25 mol % Fe(OTf)₃ (with respect to glucose), in boiling ethanol, for 12 hours. The ethanol was then removed by evaporation. Water was added and the mixture was subsequently extracted with an organic solvent. Removal of solvent gave rise to an 88% yield of the bis-furan isopropyl ester.

Example 11

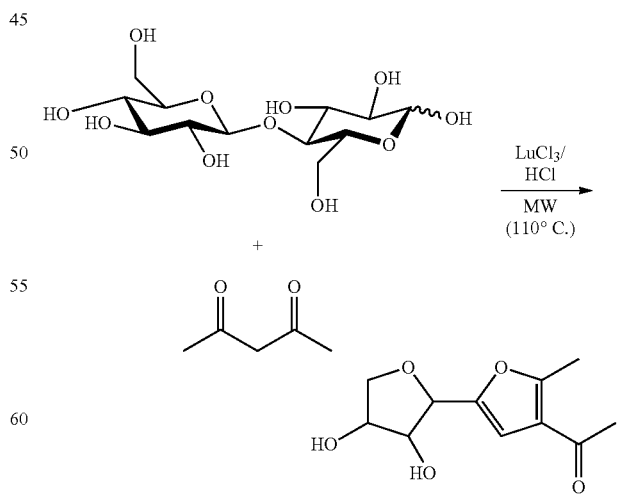

Method A: The dicarbonyl (1.266 mmol, 2.2 equivalent) was combined with the disaccharide (0.575 mmol, 1.0 equivalent), lutetium (III) trichloride (0.163 mmol, 0.3 equivalent), and 0.5 M HCl (0.35 mL), in 3.0 mL of water. The mixture was subjected to microwave conditions at 110° C. for 4 hours. Purification by silica gel chromatography gave rise to a mixture of the depicted compound and a compound of molecular weight 208 in 95% overall yield.

Method B: The dicarbonyl, water, HCl, LuCl$_3$, and the disaccharide was combined and the mixture was processed under microwave conditions at 110° C. for 4 hours. The mixture of the of the depicted compound and a compound of molecular weight 208 was obtained in 95% yield.

While certain exemplary embodiments of the present disclosure have been illustrated and described, those of ordinary skill in the art will recognize that various changes and modifications can be made to the described embodiments without departing from the spirit and scope of the present invention, and equivalents thereof, as defined in the claims that follow this description. For example, although certain components may have been described in the singular, i.e., "a" source material, "a" dicarbonyl, and the like, one or more of these components in any combination can be used according to the present disclosure.

Also, although certain embodiments have been described as "comprising" or "including" the specified components, embodiments "consisting essentially of" or "consisting of" the listed components are also within the scope of this disclosure. For example, while embodiments of the present invention are described as comprising combining a source material with a dicarbonyl, and adding hydrogen and a hydrogenation catalyst, embodiments consisting essentially of or consisting of these actions are also within the scope of this disclosure. Accordingly, a process of preparing a saturated hydrocarbon may consist essentially of combining a source material with a dicarbonyl, and adding hydrogen and a hydrogenation catalyst. In this context, "consisting essentially of" means that any additional components or process actions will not materially affect the product produced by the reaction.

As used herein, unless otherwise expressly specified, all numbers such as those expressing values, ranges, amounts or percentages may be read as if prefaced by the word "about," even if the term does not expressly appear. Further, the word "about" is used as a term of approximation, and not as a term of degree, and reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. For example, while the present disclosure may describe "a" source material or "a" dicarbonyl, a mixture of such source materials or dicarbonyls can be used. When ranges are given, any endpoints of those ranges and/or numbers within those ranges can be combined within the scope of the present disclosure. The terms "including" and like terms mean "including but not limited to," unless specified to the contrary.

Notwithstanding that the numerical ranges and parameters set forth herein may be approximations, numerical values set forth in the Examples are reported as precisely as is practical. Any numerical value, however, inherently contains certain errors necessarily resulting from the standard variation found in their respective testing measurements. The word "comprising" and variations thereof as used in this description and in the claims do not limit the disclosure to exclude any variants or additions.

What is claimed is:

1. A process of preparing a saturated hydrocarbon comprising:
    combining a source material with a dicarbonyl under conditions suitable to form an intermediate mixture, the source material comprising a depolymerized oligosaccharide mixture, a monomeric sugar, a hydrolysate, or a mixture of monomeric sugars; and
    adding hydrogen and a hydrogenation catalyst to the intermediate mixture under conditions suitable to form the saturated hydrocarbon.

2. The process of claim 1, wherein the dicarbonyl is methyl acetoacetate, ethyl acetoacetate, i-propyl acetoacetate, 2,4-pentanedione, n-propyl acetoacetate, malonate esters, cyanoacetates, or a mixture thereof.

3. The process of claim 2, wherein the dicarbonyl is 2,4-pentanedione.

4. The process of claim 1, wherein the saturated hydrocarbon is 3-ethylnonane.

5. The process of claim 1, wherein the hydrogenation catalyst is palladium/carbon or nickel.

6. The process of claim 1, wherein the source material comprises a depolymerized oligosaccharide mixture, and the depolymerized oligosaccharide mixture is prepared by heating an oligosaccharide for a time sufficient to form the depolymerized oligosaccharide mixture.

7. The process of claim 6, wherein the heating is achieved using microwave radiation.

8. The process of claim 6, wherein the heating of the oligosaccharide to form the depolymerized oligosaccharide mixture is under acidic conditions.

9. The process of claim 8, wherein the acidic conditions are achieved using hydrochloric acid, triflic acid, acetic acid, trifluoroacetic acid, or a combination thereof.

10. The process of claim 6, wherein the heating of the oligosaccharide to form the depolymerized oligosaccharide mixture is conducted in the presence of a Lewis acid catalyst or a Bronsted acid catalyst.

11. The process of claim 10, wherein the Lewis acid catalyst or the Bronsted acid catalyst is cerium chloride, iron chloride, lanthanum triflate, iron triflate, or a mixture thereof.

12. The process of claim 1, wherein the combining of the source material with the dicarbonyl is conducted in the presence of a Lewis acid catalyst or a Bronsted acid catalyst.

13. The process of claim 12, wherein the Lewis acid catalyst or the Bronsted acid catalyst is cerium chloride, iron chloride, lanthanum triflate, iron triflate, or a mixture thereof.

14. The process of claim 1, wherein the source material comprises a hydrolysate, the hydrolysate comprising a mixture of two or more sugars.

15. The process of claim 14, wherein the mixture of two or more sugars comprises a mixture of two or more of glucose, xylose, arabinose, cellobiose, galactose and/or fructose.

16. The process of claim 14, wherein the hydrolysate further comprises one or more acids.

17. The process of claim 16, wherein the one or more acids comprises one or more of lactic acid, glycerol, ethanol, acetic acid, ethanol, furfural and/or hydroxymethylfurfural (HMF).

18. The process of claim 1, wherein the monomeric sugar comprises glucose or xylose.

19. The process of claim 1, wherein the mixture of monomeric sugars comprises at least glucose and xylose.

* * * * *